United States Patent [19]

Lautenschläger et al.

[11] Patent Number: 4,507,298

[45] Date of Patent: Mar. 26, 1985

[54] 6-{4-(ω-(1-IMIDAZOLYL)-ALKYL-PHENYL}-3-OXO-2,3,4,5-TETRAHYDRO-PYRIDAZINES AND ACID ADDITION SALTS THEREOF, AND A PROCESS FOR THE TREATMENT OF INFLAMMATORY, ATHEROSCLEROTIC AND THROMBOEMBOLIC ILLNESSES IN HUMANS

[75] Inventors: Hans-Heiner Lautenschläger, Pulheim-Stommeln; Gerd Hilboll, Cologne; Hugo Friehe, Erftstadt-Lechenich; Josef P. Löhr, Hilden, all of Fed. Rep. of Germany

[73] Assignee: A. Nattermann & Cie GmbH, Cologne, Fed. Rep. of Germany

[21] Appl. No.: 397,091

[22] Filed: Jul. 12, 1982

[30] Foreign Application Priority Data

Jul. 31, 1981 [DE] Fed. Rep. of Germany ....... 3130251

[51] Int. Cl.³ .............. C07D 403/10; A61K 31/415; A61K 31/50
[52] U.S. Cl. .................................. 514/247; 544/238
[58] Field of Search ................ 544/238, 239; 424/250

[56] References Cited

U.S. PATENT DOCUMENTS

| | | | |
|---|---|---|---|
| 3,787,415 | 1/1974 | Draber et al. | 544/238 |
| 3,845,050 | 10/1974 | Lebkuechev et al. | 544/239 |
| 4,251,658 | 2/1981 | Szilagyi et al. | 424/250 |
| 4,353,905 | 10/1982 | Sircar et al. | 544/239 |

Primary Examiner—Paul M. Coughlan, Jr.
Assistant Examiner—William A. Teoli, Jr.
Attorney, Agent, or Firm—Pearne, Gordon, Sessions, McCoy, Granger & Tilberry

[57] ABSTRACT

The invention relates to new 6-{4-(ω-(1-imidazolyl)-alkyl)-phenyl}-3-oxo-2,3,4,5-tetrahydro-pyridazines having the general formula I

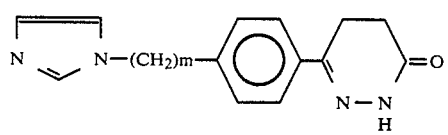

and acid addition salts thereof, and to a process for the treatment of inflammatory, atherosclerotic and thromboembolic diseases especially in humans.

13 Claims, No Drawings

6-{4-(ω-(1-IMIDAZOLYL)-ALKYL-PHENYL}-3-OXO-2,3,4,5-TETRAHYDRO-PYRIDAZINES AND ACID ADDITION SALTS THEREOF, AND A PROCESS FOR THE TREATMENT OF INFLAMMATORY, ATHEROSCLEROTIC AND THROMBOEMBOLIC ILLNESSES IN HUMANS

The present invention relates to new 6-{4-[ω-(1-imidazolyl)-alkyl]-phenyl}-3-oxo-2,3,4,5-tetrahydro-pyridazines and acid addition salts thereof, and to a process for the preparation of these compounds, and their use as the active compound in medicaments, in particular for the treatment of inflammatory and thrombo-embolic illnesses. The 6-{4-[ω-(1-imidazolyl)-alkyl]-phenyl}-3-oxo-2,3,4,5-tetrahydro-pyridazines according to the invention correspond to the general formula I

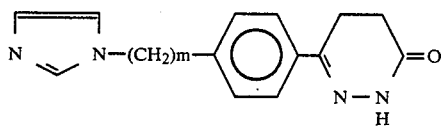

wherein m is an integer from 1 to 12, in particular 1 to 5; acid addition salts of the formula I are also included. Acid addition salts are, in particular, pharmaceutically useful, non-toxic acid addition salts with inorganic acids, for example hydrochloric acid, hydrobromic acid, sulphuric acid or phosphoric acid, or with organic acids, such as appropriate carboxylic acids, for example acetic acid, propionic acid, oxalic acid, malonic acid, glycolic acid, succinic acid, maleic acid, fumaric acid, malic acid, tartaric acid, citric acid, benzoic acid or cinnamic acid.

The compounds of the present invention have valuable pharmacological properties. On the one hand, they are distinguished by their powerful influence on the metabolism of arachidonic acid, and on the other hand they display an antagonistic action in respect of some physiological processes controlled by PAF (platelet activating factor). The compounds according to the invention therefore or moreover have a powerful anti-thrombotic, antiatherosclerotic and antirheumatic activity. In addition, the compounds of the general formula I have a favourable influence on asthmatic complaints as well as blood pressure-regulating properties. They can be used, in particular, for the treatment of inflammatory, atherosclerotic and thrombo-embolic illnesses, especially in humans.

The substances according to the invention are prepared by reacting 4-{4-[ω-(1-imidazolyl)-alkyl]-phenyl}-4-oxo-butyric acids or esters thereof of the formula II with hydrazine or its hydrate or salts, such as the hydrochloride, hydrosulphate and the like, in aqueous, aqueous-alcoholic or alcoholic media or in inert organic solvents, such as, for example, toluene or mixtures thereof with water or alcohol, at temperatures of from 0° to 150° C., preferably in ethanol or water. If appropriate, the reaction can be catalysed by acids, which can be used in the form of their hydrazinium salts, or by bases, such as, for example, alkaline earth metal oxides.

The reaction is illustrated by the following equation:

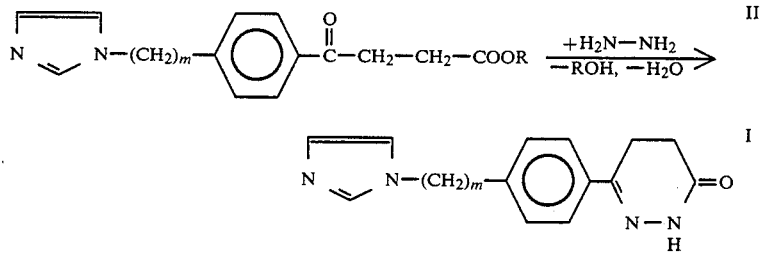

Possible starting compounds of the formula II are, in particular: 4-[4-(1-imidazolylmethyl)-phenyl]-4-oxo-butyric acid and $C_{1-6}$-alkyl esters thereof; 4-{4-[2-(1-imidazolyl)-ethyl]-phenyl}-4-oxo-butyric acid and $C_{1-6}$-alkyl esters thereof; 4-{4-[3-(1-imidazolyl)-propyl]-phenyl}-4-oxo-butyric acid and $C_{1-6}$-alkyl esters thereof; 4-{4-[4-(1-imidazolyl)-butyl]-phenyl}-4-oxo-butyric acid and $C_{1-6}$-alkyl esters thereof; 4-{4-[5-(1-imidazolyl)-pentyl]-phenyl}-4-oxo-butyric acid and $C_{1-6}$-alkyl esters thereof; 4-{4-[6-(1-imidazolyl)-hexyl]-phenyl}-4-oxo-butyric acid and $C_{1-6}$-alkyl esters thereof; 4-{4-[7-(1-imidazolyl)-heptyl]-phenyl}-4-oxo-butyric acid and $C_{1-6}$-alkyl esters thereof; 4-{4-[8-(1-imidazolyl)-octyl]-phenyl}-4-oxo-butyric acid and $C_{1-6}$-alkyl esters thereof; 4-{4-[9-(1-imidazolyl)-nonyl]-phenyl}-4-oxo-butyric acid and $C_{1-6}$-alkyl esters thereof; 4-{4-[10-(1-imidazolyl)-decyl]-phenyl}-4-oxo-butyric acid and $C_{1-6}$-alkyl esters thereof; 4-{4-[11-(1-imidazolyl)-undecyl]-phenyl}-4-oxo-butyric acid and $C_{1-6}$-alkyl esters thereof and 4-{4-[12-(1-imidazolyl)-dodecyl]-phenyl}-4-oxo-butyric acid and $C_{1-6}$-alkyl esters thereof.

The starting compounds of the formula II are prepared by processes which are known per se: 1-(ω-phenylalkyl)-imidazoles are prepared by alkylation of imidazole with the corresponding ω-halogenoalkylbenzene, if appropriate with the addition of an organic solvent, such as, for example, dimethylformamide, and with the possible use of an auxiliary base, such as, for example, sodium hydride British Patent Application No. 2,031,408. The 1-(ω-phenylalkyl)-imidazoles are reacted with a succinic acid alkyl ester chloride, with the addition of an organic solvent, such as, for example, 1,2-dichloroethane, nitrobenzene or carbon disulphide, using a Friedel-Crafts catalyst, such as, for example, aluminium chloride, by processes familiar to the expert (Houben-Weyl, Methoden der organischen Chemie (Methods of Organic Chemistry), Volume 7/2a, page 257 et seq.) to give the 4-{4-[ω-(1-imidazolyl)-alkyl]-phenyl}-4-oxo-butyric acid alkyl esters.

The acid addition salts of compounds of the formula I with inorganic or organic acids can be prepared by mixing the imidazolyl compounds on which they are based with the corresponding acids in aqueous, aqueous-organic (for example alcohol/water) or organic media, such as, for example, alcohols, alcohol/ether mixtures or ether/petroleum ether mixtures, at temperatures between 0° and 100° C.

The present invention also relates to pharmaceutical products which contain compounds of the formula I or pharmaceutically usable acid addition salts of these compounds. The pharmaceutical products according to the invention are products for enteral, such as oral or rectal, or parenteral administration which contain the pharmacological active compounds by themselves or together with a customary, pharmaceutically usable excipient.

Advantageously, the pharmaceutical formulation of the active compound is in the form of individual doses appropriate for the desired administration, such as, for example, tablets, dragees, capsules, suppositories, granules, solutions, emulsions or suspensions. The dosage of the compound is usually between 1 and 500 mg per dose, preferably between 5–150 mg per dose, and can be administered once or several times, preferably two to three times, daily. The preparation of the compound according to the invention is illustrated in more detail by the examples which follow. The melting points given were measured with a Büchi 510 melting point determination apparatus, and are given in °C. and are uncorrected. The IR spectra were recorded with a Perkin Elmer 257 apparatus and the mass spectra with a Varian MAT-311-A (70eV) apparatus.

EXAMPLE 1

6-[4-(1-Imidazolylmethyl)-phenyl]-3-oxo-2,3,4,5-tetrahydro-pyridazine.

A mixture of 7.7 g of 4-[4-(1-imidazolylmethyl)-phenyl]-4-oxo-butyric acid methyl ester, 0.2 g of barium oxide, 1.4 g of hydrazine hydrate and 30 ml of ethanol is stirred at 0° C. for 10 minutes and then at room temperature for 2 hours, and is subsequently heated under reflux for 1 hour. The reaction solution is diluted with water and extracted with chloroform and the extract is washed with water and dried over $Na_2SO_4$. The solvent is stripped off and the residue which remains is purified by stirring with ether.

Yield: 2.4 g, melting point: 225° C.; IR(in KBr): 1,675 $cm^{-1}$; MS [m/e]: 254 ($M^+$, 40%), 187 (100%) and 116 (21%).

EXAMPLE 2

6-{4-[2-(1-Imidazolyl)-ethyl]-phenyl}-3-oxo-2,3,4,5-tetrahydro-pyridazine

A mixture of 7.5 g of 4-{4-[2-(1-imidazolyl)-ethyl]-phenyl}-4-oxo-butyric acid methyl ester, 0.2 g of barium oxide, 1.3 g of hydrazine hydrate and 30 ml of ethanol is stirred at 0° C. for 10 minutes and then at room temperature for 2 hours, and is subsequently heated under reflux for 1 hour. The reaction mixture is diluted with water and extracted with chloroform and the extract is washed with water and dried over $Na_2SO_4$. The solvent is stripped off and the residue is purified by column chromatography (silica gel/chloroform/methanol).

Yield: 3.6 g, melting point: 145° C.; IR (in KBr): 1,660 $cm^{-1}$; MS [m/e]: 268 ($M^+$, 100%), 187 (67%), 116 (17%) and 81 (22%).

EXAMPLE 3

6-{4-[3-(1-Imidazolyl)-propyl]-phenyl}-3-oxo-2,3,4,5-tetrahydro-pyridazine 2 g of 4-{4-[3-(1-imidazolyl)-propyl]-phenyl}-4-oxo-butyric acid are suspended in 10 ml of water, 0.68 g of hydrazine hydrate are added and the mixture is then stirred at 90° C. for 2 hours. After the mixture has been cooled, it is extracted with chloroform and the chloroform solution is washed with water, dried over $Na_2SO_4$ and concentrated to dryness.

Yield: 1.2 g, melting point: 136° C.; IR (in KBr): 1,675 $cm^{-1}$; MS [m/e]: 282 ($M^+$, 100%), 266 (0.7%), 253 (10%), 240 (13%), 212 (11%) and 186 (10%).

EXAMPLE 4

6-{4-[4-(1-Imidazolyl)-butyl]-phenyl}-3-oxo-2,3,4,5-tetrahydro-pyridazine.

(a) From 4-{4-[4-(1-imidazolyl)-butyl]-phenyl}-4-oxo-butyric acid methyl ester

A mixture of 10 g of the ester, 0.4 g of barium oxide, 1.58 g of hydrazine hydrate and 30 ml of ethanol is stirred at 0° C. for 10 minutes and then at room temperature for 20 hours, and is heated under reflux for another 6 hours. After the mixture has been cooled, the solvent is stripped off and the residue is taken up in water and extracted with chloroform. The chloroform phase is washed with water, dried over $Na_2SO_4$ and concentrated. The residue is purified by column chromatography (silica gel/chloroform/methanol).

Yield: 3.9 g, melting point: 131° C.; IR (in KBr): 1,675 $cm^{-1}$; MS [m/e]: 296 ($M^+$, 100%), 267 (15%), 254 (16%), 226 (18%), 200 (10%), 69 (35%).

(b) From 4-{4-[4-(1-imidazolyl)-butyl]-phenyl}-4-oxo-butyric acid.

1.5 g of the acid are suspended in 10 ml of water. After addition of 0.3 g of hydrazine hydrate, the mixture is stirred at 90° C. for 2 hours. After the mixture has been cooled, it is extracted with chloroform and the chloroform phase is washed with water, dried over $Na_2SO_4$ and concentrated to dryness.

Yield: 1.25 g, melting point: 129°–131° C.

EXAMPLE 5

6-{4-[5-(1-Imidazolyl)-pentyl]-phenyl}-3-oxo-2,3,4,5-tetrahydro-pyridazine.

(a) From 4-{4-[5-(1-imidazolyl)-pentyl]-phenyl}-4-oxo-butyric acid methyl ester.

A mixture of 10.5 g of the ester, 0.4 g of barium oxide, 1.58 g of hydrazine hydrate and 30 ml of ethanol is stirred at 0° C. for 10 minutes and then at room temperature for 18 hours, and is heated under reflux for another 4 hours. After the mixture has been cooled, the solvent is stripped off and the residue is taken up in water and extracted with chloroform. The chloroform phase is washed with water, dried over $Na_2SO_4$ and concentrated. The residue is purified by column chromatography (silica gel/chloroform/methanol).

Yield: 2.3 g, melting point 124° C.; IR (in KBr): 1,680 $cm^{-1}$; MS [m/e]: 310 ($M^+$, 48%), 294 (3%), 281 (16%), 268 (10%), 240 (57%), 214 (23%) and 69 (100%).

(b) From 4-}4-[5-(1-imidazolyl)-pentyl]-phenyl}-4-oxo-butyric acid.

3.14 g of the acid are suspended in 10 ml of water. After addition of 0.6 g of hydrazine hydrate, the mixture is stirred at 90° C. for 2 hours. After the mixture has been cooled, it is filtered with suction and the residue is washed with water and dried.

Yield: 2.56 g, melting point: 124°–126° C.

PREPARATION OF THE STARTING COMPOUND

4-{4-[4-(1-Imidazolyl)-butyl]-phenyl}-4-oxo-butyric acid methyl ester 20.3 g of succinic acid methyl ester chloride and then a solution of 27 g of 1-(4-phenylbutyl)-imidazole in 100 ml of 1,2-dichloroethane are added dropwise to a suspension of 59.3 g of aluminium chloride in 200 ml of 1,2-dichloroethane, whilst cooling with ice. The mixture is then stirred at 85° C. for 3 hours. After it has been cooled, the reaction mixture is stirred into a mixture of 165.7 g of ethylenediaminetetraacetic acid and 600 g of ice and is brought to about pH 8 by addition of dilute sodium hydroxide solution. The phases are separated and the organic phase is dried over $Na_2SO_4$ and concentrated. The residue is purified by column chromatography (silica gel/chloroform).

Yield: 32 g, melting point 53°–54° C.; IR (in KBr): 1,730 and 1,680 cm$^{-1}$; MS [m/e]: 314 (M+, 25%), 283 (14%), 255 (21%), 227 (100%), 200 (15%), 131 (16%) and 96 (66%)

4-{4-[4-(1-Imidazolyl)-butyl]phenyl}-4-oxo-butyric acid.

15 g of 4-{4-[4-(1-imidazolyl)-butyl]-phenyl}-4-oxo-butyric acid methyl ester are dissolved in 180 ml of methanol, and 2.3 g of sodium hydroxide, dissolved in a little methanol, are added. The mixture is stirred at room temperature for 24 hours, the solvent is stripped off and the residue is taken up in water. The solution is extracted several times with chloroform and the chloroform phase is discarded. The aqueous solution is adjusted to about pH 6 with dilute hydrochloric acid and the solid which has precipitated is filtered off with suction, washed with a little water and dried.

Yield: 8.8 g, melting point: 165°–166° C.; IR (in KBr): 1,710 and 1,680 cm$^{-1}$; MS [m/e]: 299 (M+−1, 0.5%), 282 (4%), 256 (13%), 227 (35%), 200 (100%), 131 (18%), 96 (28%), 82 (28%) and 69 (33%).

The following compounds are prepared analogously to Examples 1–5;

6. 6-{4-[6-(1-Imidazolyl)-hexyl]-phenyl}-3-oxo-2,3,4,5-tetrahydro-pyridazine
7. 6-{4-[7-(1-Imidazolyl)-heptyl]-phenyl}-3-oxo-2,3,4,5-tetrahydro-pyridazine
8. 6-{4-[8-(1-Imidazolyl)-octyl]-phenyl}-3-oxo-2,3,4,5-tetrahydro-pyridazine
9. 6-{4-[9-(1-Imidazolyl)-nonyl]-phenyl}-3-oxo-2,3,4,5-tetrahydro-pyridazine
10. 6-{4-[10-(1-Imidazolyl)-decyl]-phenyl}-3-oxo-2,3,4,5-tetrahydro-pyridazine
11. 6-{4-[11-(1-Imidazolyl)-undecyl]-phenyl}-3-oxo-2,3,4,5-tetrahydro-pyridazine
12. 6-{4-[12-(1-Imidazolyl)-dodecyl]-phenyl}-3-oxo-2,3,4,5-tetrahydro-pyridazine

EXAMPLE 13

The fumaric acid salt of 6-{4-[5-(1-imidazolyl)-pentyl]-phenyl}-3-oxo-2,3,4,5-tetrahydro-pyridazine A mixture of 1.5 g of 6-{4-[5-(1-imidazolyl)-pentyl]-phenyl}-3-oxo-2,3,4,5-tetrahydro-pyridazine and 0.55 g of fumaric acid in 30 ml of ethanol is heated under reflux for about 30 minutes, until a clear solution has formed. When the solution is cooled, the salt crystallises out, and is filtered off with suction and dried.

Yield: 1.73 g, melting point: 138° C.; IR (in KBr): 1,680 cm$^{-1}$.

Oxalates, succinates, malonates and the like and inorganic salts, such as hydrochlorides, hydrosulphates and the like, can be prepared, for example, analogously to Example 13.

What we claim is:

1. 6-{4-[ω-(1-Imidazolyl)-alkyl]-phenyl}-3-oxo-2,3,4,5-tetrahydro-pyridazines of the formula I

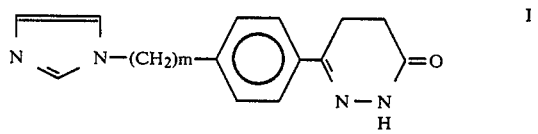

in which m denotes an integer from 1 to 12, and acid addition salts thereof with inorganic or organic acids.

2. 6-[4-(1-Imidazolylmethyl)-phenyl]-3-oxo-2,3,4,5-tetrahydro-pyridazine and pharmaceutically acceptable salts thereof.

3. 6-{4-[2-(1-Imidazolyl)-ethyl]-phenyl}-3-oxo-2,3,4,5-tetrahydro-pyridazine and pharmaceutically acceptable salts thereof.

4. 6-{4-[3-(1-Imidazolyl)-propyl]-phenyl}-3-oxo-2,3,4,5-tetrahydro-pyridazine and pharmaceutically acceptable salts thereof.

5. 6-{4-[4-(1-Imidazolyl)-butyl]-phenyl}-3-oxo-2,3,4,5-tetrahydro-pyridazine and pharmaceutically acceptable salts thereof.

6. 6-{4-[5-(1-Imidazolyl)-pentyl]-phenyl}-3-oxo-2,3,4,5-tetrahydro-pyridazine and pharmaceutically acceptable salts thereof.

7. 6-{4-[6-(1-Imidazolyl)-hexyl]-phenyl}-3-oxo-2,3,4,5-tetrahydro-pyridazine and pharmaceutically acceptable salts thereof.

8. 6-{4-[7-(1-Imidazolyl)-heptyl]-phenyl}-3-oxo-2,3,4,5-tetrahydro-pyridazine and pharmaceutically acceptable salts thereof.

9. 6-{4-[8-(1-Imidazolyl)-octyl]-phenyl}-3-oxo-2,3,4,5-tetrahydro-pyridazine and pharmaceutically acceptable salts thereof.

10. 6-{4-[9-(1-Imidazolyl)-nonyl]-phenyl}-3-oxo-2,3,4,5-tetrahydro-pyridazine and pharmaceutically acceptable salts thereof.

11. 6-{4-[10-(1-Imidazolyl)-decyl]-phenyl}-3-oxo-2,3,4,5-tetrahydro-pyridazine and pharmaceutically acceptable salts thereof.

12. 6-{4-[11-(1-Imidazolyl)-undecyl]-phenyl}-3-oxo-2,3,4,5-tetrahydro-pyridazine and pharmaceutically acceptable salts thereof.

13. 6-{4-[12-(1-Imidazolyl)-dodecyl]-phenyl}-3-oxo-2,3,4,5-tetrahydro-pyridazine and pharmaceutically acceptable salts thereof.

* * * * *

UNITED STATES PATENT AND TRADEMARK OFFICE
CERTIFICATE OF CORRECTION

PATENT NO. : 4,507,298
DATED : March 26, 1985
INVENTOR(S) : Hans-Heiner Lautenschlager et al.

It is certified that error appears in the above-identified patent and that said Letters Patent are hereby corrected as shown below:

On the cover page please insert the following information:

-- FOREIGN PATENT DOCUMENTS 2031408  4/1980  United Kingdom --

Column 4, line 64, change the first " } " to -- { --.

Signed and Sealed this

Tenth Day of December 1985

[SEAL]

Attest:

DONALD J. QUIGG

Attesting Officer

Commissioner of Patents and Trademarks